(12) United States Patent  
Crank et al.

(10) Patent No.: US 9,364,615 B2  
(45) Date of Patent: Jun. 14, 2016

(54) DEVICES, SYSTEMS, AND METHODS FOR DELIVERING FLUID TO TISSUE

(71) Applicants: Justin M. Crank, Maple Grove, MN (US); Suranjan Roychowdhury, Plymouth, MN (US); Carey J. Becker, Savage, MN (US)

(72) Inventors: Justin M. Crank, Maple Grove, MN (US); Suranjan Roychowdhury, Plymouth, MN (US); Carey J. Becker, Savage, MN (US)

( * ) Notice: Subject to any disclaimer, the term of this patent is extended or adjusted under 35 U.S.C. 154(b) by 0 days.

(21) Appl. No.: 14/153,709

(22) Filed: Jan. 13, 2014

(65) Prior Publication Data

US 2014/0128805 A1      May 8, 2014

Related U.S. Application Data

(62) Division of application No. 13/260,869, filed as application No. PCT/US2010/042591 on Jul. 20, 2010, now Pat. No. 8,628,494.

(60) Provisional application No. 61/226,855, filed on Jul. 20, 2009, provisional application No. 61/226,849, filed on Jul. 20, 2009, provisional application No. 61/226,832, filed on Jul. 20, 2009, provisional application No. 61/226,805, filed on Jul. 20, 2009, provisional application No. 61/226,796, filed on Jul. 20, 2009.

(51) Int. Cl.
```
A61M 5/30       (2006.01)
A61M 25/00      (2006.01)
A61M 31/00      (2006.01)
A61M 25/04      (2006.01)
```

(52) U.S. Cl.
CPC ............... *A61M 5/30* (2013.01); *A61M 25/007* (2013.01); *A61M 25/0054* (2013.01); *A61M 31/00* (2013.01); *A61M 25/005* (2013.01); *A61M 25/04* (2013.01); *A61M 2210/1078* (2013.01)

(58) Field of Classification Search
CPC .......... A61M 25/007; A61M 25/0068; A61M 2025/0057
USPC ............................................... 604/43, 103.01
See application file for complete search history.

(56) References Cited

U.S. PATENT DOCUMENTS

| | | |
|---|---|---|
| 4,093,108 A | 6/1978 | Hein et al. |
| 4,130,119 A | 12/1978 | Sessions et al. |
| 4,742,817 A | 5/1988 | Kawashima et al. |
| 4,946,442 A | 8/1990 | Sanagi |

(Continued)

FOREIGN PATENT DOCUMENTS

| | | |
|---|---|---|
| WO | WO 92/00774 | 1/1992 |
| WO | WO9616606 A1 | 6/1996 |

(Continued)

*Primary Examiner* — Gerald Landry, II  
(74) *Attorney, Agent, or Firm* — Kagan Binder, PLLC

(57) ABSTRACT

A needleless fluid injection device including a flexible shaft with a proximal end, a distal end, an injection lumen extending from the proximal end to the distal end of the shaft, and at least one injection orifice extending through a wall of the injection lumen at the distal end of the shaft. The injection lumen can include a depth-limiting system (462) at its distal end for controlling the depth of insertion of the injection lumen relative to a target tissue of a patient. The injection lumen can alternatively or additionally include at least one guidance feature. The injection lumen can alternatively or additionally include at least one flow-modifying protrusion extending from the inner tubular wall of the injection lumen and toward a longitudinal axis of the injection lumen.

12 Claims, 5 Drawing Sheets

(56) References Cited

U.S. PATENT DOCUMENTS

| | | | |
|---|---|---|---|
| 5,007,897 A * | 4/1991 | Kalb et al. ..................... 604/43 |
| 5,116,313 A | 5/1992 | McGregor |
| 5,261,889 A | 11/1993 | Laine et al. |
| 5,336,178 A | 8/1994 | Kaplan |
| 5,423,750 A * | 6/1995 | Spiller .......................... 604/80 |
| 5,693,016 A | 12/1997 | Gumaste et al. |
| 5,840,062 A | 11/1998 | Gumaste et al. |
| 6,203,533 B1 | 3/2001 | Ouchi |
| 6,210,378 B1 | 4/2001 | Ouchi |
| 6,217,549 B1 | 4/2001 | Selmon et al. |
| 6,238,336 B1 | 5/2001 | Ouchi |
| 6,280,413 B1 * | 8/2001 | Clark .................... A61F 2/013 604/102.01 |
| 6,400,980 B1 | 6/2002 | Lemelson |
| 6,537,205 B1 | 3/2003 | Smith |
| 6,547,767 B1 | 4/2003 | Moein |
| 6,558,349 B1 | 5/2003 | Kirkman |
| 6,599,267 B1 * | 7/2003 | Ray et al. ................ 604/102.01 |
| 6,641,553 B1 | 11/2003 | Chee et al. |
| 6,663,589 B1 * | 12/2003 | Halevy ....................... 604/96.01 |
| 6,709,386 B2 | 3/2004 | Smid et al. |
| 6,716,190 B1 | 4/2004 | Glines et al. |
| 6,905,475 B2 | 6/2005 | Hauschild et al. |
| 7,594,900 B1 * | 9/2009 | Nash ................ A61B 17/32037 604/27 |
| 7,749,156 B2 | 7/2010 | Ouchi |
| 7,933,290 B2 * | 4/2011 | Aholainen ................... 370/466 |
| 8,137,337 B2 | 3/2012 | Hakky et al. |
| 2001/0007059 A1 * | 7/2001 | Mirzaee .................. 604/164.03 |
| 2002/0058961 A1 | 5/2002 | Aguilar et al. |
| 2003/0163111 A1 | 8/2003 | Daellenbach |
| 2003/0171641 A1 | 9/2003 | Schweich et al. |
| 2004/0030320 A1 | 2/2004 | Chee et al. |
| 2004/0162528 A1 | 8/2004 | Horvath et al. |
| 2005/0192530 A1 | 9/2005 | Castellano |
| 2005/0228225 A1 | 10/2005 | Hauschild et al. |
| 2006/0129125 A1 | 6/2006 | Copa et al. |
| 2007/0167921 A1 | 7/2007 | Burren et al. |
| 2007/0225554 A1 | 9/2007 | Maseda et al. |
| 2008/0114203 A1 | 5/2008 | Crank |
| 2008/0119784 A1 | 5/2008 | Roychowdhury |
| 2008/0119823 A1 | 5/2008 | Crank |
| 2009/0048577 A1 * | 2/2009 | Gillies ................. A61B 5/0084 604/510 |
| 2009/0124974 A1 | 5/2009 | Crank et al. |
| 2009/0259126 A1 * | 10/2009 | Saal et al. ..................... 600/433 |
| 2009/0312696 A1 * | 12/2009 | Copa .................... A61M 25/007 604/43 |
| 2010/0069781 A1 * | 3/2010 | Johansen et al. ............... 600/547 |
| 2010/0228178 A1 * | 9/2010 | McGraw ............. A61M 1/3653 604/6.16 |
| 2011/0015614 A1 | 1/2011 | Rykhus, Jr. et al. |
| 2011/0046600 A1 * | 2/2011 | Crank .......................... 604/500 |
| 2011/0295214 A1 * | 12/2011 | Pugh .................... A61M 25/007 604/195 |

FOREIGN PATENT DOCUMENTS

| | | |
|---|---|---|
| WO | WO9736625 A1 | 10/1997 |
| WO | WO0040279 A1 | 7/2000 |
| WO | WO0066199 A1 | 11/2000 |
| WO | WO0136029 A1 | 5/2001 |
| WO | WO0207812 A2 | 1/2002 |
| WO | WO2004071612 A2 | 8/2004 |
| WO | WO2005094921 A1 | 10/2005 |
| WO | WO 2006/055826 | 5/2006 |
| WO | WO2006057604 A1 | 6/2006 |
| WO | WO2006063180 A2 | 6/2006 |
| WO | WO2006076699 A1 | 7/2006 |
| WO | WO2006084821 A2 | 8/2006 |
| WO | WO2006086719 A2 | 8/2006 |
| WO | WO2007038591 A2 | 4/2007 |
| WO | WO2007079152 A2 | 7/2007 |
| WO | WO2010065126 A2 | 6/2010 |
| WO | WO2010065127 A2 | 6/2010 |
| WO | WO2010065133 A2 | 6/2010 |
| WO | WO2010074705 A2 | 7/2010 |
| WO | WO2010077271 A2 | 7/2010 |
| WO | WO2011011423 A1 | 1/2011 |

* cited by examiner

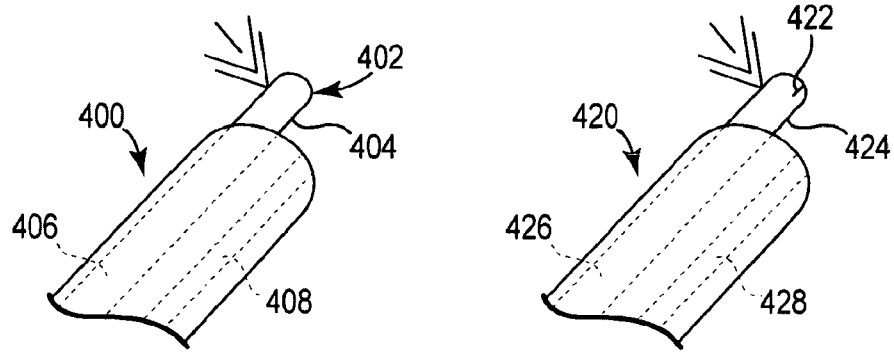
Fig. 4  Fig. 5
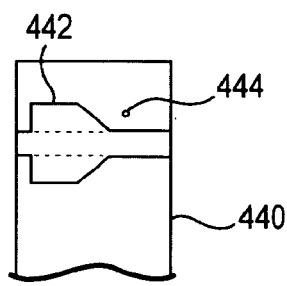 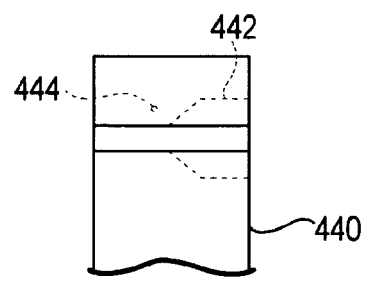
Fig. 6  Fig. 7

DEVICES, SYSTEMS, AND METHODS FOR DELIVERING FLUID TO TISSUE

CROSS-REFERENCE TO RELATED APPLICATION

This application is a divisional application of U.S. patent application Ser. No. 13/260,869, filed Nov. 18, 2011, which claims the benefit from International Application No. PCT/US2010/042591, filed Jul. 20, 2010, which in turn claims priority under 35 U.S.C. §119(e) to U.S. Provisional Application No. 61/226,805, filed Jul. 20, 2009, titled, "High-Pressure Flow Distribution Injection System and Method"; U.S. Provisional Application No. 61/226,832, filed Jul. 20, 2009, titled, "High-Pressure Injection System and Method"; U.S. Provisional Application No. 61/226,849, filed Jul. 20, 2009, titled, "Depth Limiting High-Pressure Injection System and Method"; U.S. Provisional Application No. 61/226,855, filed Jul. 20, 2009, titled, "High-Pressure Polymer Injection System and Method"; and U.S. Provisional Application No. 61/226,796, filed Jul. 20, 2009, titled, "Injection Catheter and Guidance System and Method", the entire contents of which are all incorporated herein by reference in their entireties.

TECHNICAL FIELD

The present invention relates generally to the delivery of therapeutic fluids to a treatment site within a patient. More specifically, the invention relates to methods and devices for treating tissue within the human body using a pressurized injection system that accurately delivers therapeutic fluids to a desired location, such as the urinary tract of a patient.

BACKGROUND

A wide variety of medical treatments utilize the delivery and introduction of therapeutic compositions to a treatment location in a patient. In home or outpatient settings, the delivery methods used can include procedures such as oral delivery or inhalants, while in clinical or hospital types of settings, a therapeutic fluid is often injected using a needle-based system. In more complicated methods, a fluid can be delivered surgically through a tubular device, such as a catheter or endoscope, and in some cases, the surgical method can involve minimally invasive procedures.

For minimally invasive procedures, a number of systems have been developed for delivering therapeutic fluids to treatment sites within a patient that include minimally invasive, tubular delivery lumens (e.g., catheters or endoscopes) and pressurized fluid sources. In some cases, these fluid sources include a syringe-like structure that is actuated by a plunger. This plunger can be controlled via a console having control features that help the user to control the amount of pressurized fluid that is delivered to and/or expelled from the system. These systems can include needleless fluid injection systems, for example. Needleless devices and methods for treating tissue of the urinary tract are discussed, for example, in U.S. Patent Application Publication No. 2009/0312696 (Copa et al.), and U.S. Patent Application Publication No. 2006/0129125 (Copa et al.), the entire disclosures of which are incorporated herein by reference. One particular application for needleless fluid delivery systems is for treatment of diseases of the prostate, such as prostatitis, benign prostatic hyperplasia, and pro static carcinoma.

Needleless fluid delivery systems can include the use of a tube-like device, such as an elongated catheter tube, which is configured to provide a jet-injection of a therapeutic fluid at a desired treatment site. Generally, a needleless injector is used to deliver the therapeutic fluid that is provided from an external reservoir that is located at a proximal end of the tube-like device. The actual fluid administration occurs at a distal end of the tube-like device. Due to the relatively long travel length of the therapeutic fluid through the tube-like device, an injector must generally be capable of pressurizing the therapeutic fluid to a relatively high pressure in order to achieve a certain desired fluid delivery pressure at the distal end of the device.

For any injection or injected tissue, therapeutic agents are desirably delivered with minimal discomfort and procedure time, and with the best possible degree of accuracy of delivery location and delivery volume, and with uniform and accurate distribution of a fluid throughout injected tissue. Further, due to the characteristics associated with the delivery of therapeutic compositions to treatment locations in a patient, there is a need to provide improved procedures, systems, and components for fluid delivery using needleless fluid delivery systems. Such procedures, systems, and components can provide for accurate and controlled dispensing of therapeutic compositions to specific treatment locations within a patient. In particular, there exists a continuing need to provide improved devices for delivering therapeutic fluids to different tissues such as locations of the urinary tract including the bladder, bladder neck, prostate, urethra, kidneys, and ureters.

SUMMARY

The invention generally involves needleless fluid injection devices, systems, and methods. These devices and systems allow for targeted delivery of therapeutic fluids at desired anatomical tissue locations, such as locations in the male or female urinary tract. The therapeutic fluids can include biologically active species and agents such as chemical and biochemical agents, for example. Exemplary devices are designed to deliver fluid at various tissue locations, and can further deliver multiple different therapeutic fluids having varying material properties (e.g., viscosity) using a single system. The devices can be capable of delivering precise amounts of fluid for injection at precise locations and at specific pressures to a location in the patient.

Embodiments of the described invention involve a fluid delivery system with an injector source and an access device. The access device can comprise a minimally invasive, tubular delivery lumen such as a catheter or endoscope. The injector source can include a non-metal, polymeric tube-like device for delivering a therapeutic fluid to a treatment site within a patient. The tube-like device can further include one or more apposing jets that can be selectively fired to force the injection orifice or orifices of the tube-like device against the target tissue. Selective firing can include a continuous firing during the injection to improve the efficiency of the treatment. The apposing jets can include nozzles or vanes to improve the ability of the operator to selectively fire the apposing jet for creating contact with the target tissue.

In various embodiments, devices as described can be useful for injecting tissue at different tissue depths and in any desired direction (relative to a surface of the injected tissue), including relatively deep injection of fluid into tissue of any size or depth, or for shallow injection of fluid into tissue at a depth near a tissue surface, such as if the tissue is of a limited depth. Depending on the desired injection depth, orifices can be oriented at different locations along a length of a shaft and at different directions or angles relative to the shaft.

Certain devices as described provide features for handling, placement, control, and accuracy of injected fluid in terms of location distribution, and volume of fluid delivery. For example, multiple injection orifices can be arranged along a length or a circumference of a shaft to cause forces produced by ejection of fluid to be balanced or otherwise controlled, relative to the shaft. In some embodiments, a net force on the shaft created by the ejection of fluid from multiple orifices at a shaft distal end can be zero. In other embodiments, a net force on a shaft created by the ejection of fluid from multiple orifices may create a force used to control the distal end of a device. A net force may be created by ejected fluid, for example, to place an injection orifice in apposition to tissue. That is, a net force can cause a shaft and an injection orifice to be pressed against a tissue surface to provide for secure engagement between the injection orifice, shaft, and tissue surface during a fluid delivery process.

In one aspect of this invention, a needleless injection device is provided that includes a flexible catheter shaft comprising a proximal end, a distal end, a distal end tip, and an injection lumen extending from the proximal end to the distal end. The distal end includes multiple injection orifices that are spaced from each other along the length and/or circumference of the injection lumen and which are in communication with the injection lumen. The shaft is capable of ejecting a fluid stream from each of the injection orifices, wherein the fluid streams are capable of being injected into tissue by penetration of a tissue surface as a fluid stream. The injection lumen further can include one or more features that are positioned within its interior area that can alter the flow of fluid, thereby providing for certain outflow characteristics. In particular, the features can be formed or shaped to include one or more interior flow features or protrusions that generally restrict and/or redirect the fluid flow through the lumen to provide for controllable distribution of flow through each of the orifices. For example, these flow features can be used to achieve certain flow rates through particular orifices, or may be used to make the flow rate relatively uniform for fluid exiting all of the orifices of one lumen.

In another aspect of the invention, an injection device and system can be configured without means for connecting or attaching an optic device, such as an endoscope, to an injection catheter, while still being able to utilize the other component features of the system, such as a delivery lumen, fluid source, apposition device, and the like. A system of this type can advantageously include additional torque control mechanisms that may be relatively difficult to incorporate or use if the system includes an optic device and its corresponding structure. The torque structures used can include a braided tube, coils, micro-machined tubes, kink-resistant tubing (KRT) features, and the like, and can be made of a number of different materials, such as metals, polymers, and ceramics.

In another aspect of the invention, a delivery lumen can include depth-limiting or depth-controlling features that can be attached or otherwise incorporated into the device. These features can help to control or limit the indentation of the distal end tip of the device when positioning the injectate ports or orifices in a desired position to promote transverse or radial injectate dispersion from the ports. This can be accomplished via an expandable and collapsible member, such as a hinging or folding plate member. The member or members can be manually or automatically deployable, such as with an actuation member that controls the expansion and/or retraction. Alternatively, the members can be constructed of a shape memory or biased material that urge the members into either an open or closed position. These members can be expandable to abut with the surrounding tissue walls of the lumen into which the device is positioned. The members may comprise various structures, mechanisms, and techniques, such as hinged members, biasing members, pop-out members, inflatable members, and the like.

In accordance with the invention, a delivery lumen and its associated components can be constructed of specific polymer materials having reinforcement features. The reinforcement can be incorporated or mixed into the polymer material or can be provided as a coating. The materials can provide additional strength to the lumen that will allow it to better withstand the pressures used with these relatively high-pressure injection catheters.

In another aspect of the invention, a device can be provided with various guidance or targeting features that can be coupled with other visualization systems (e.g., optics or an endoscope). In one particular embodiment, the injection catheter or lumen can include at least one surface indicia or marker and/or at least one protrusion that is detectable using ultrasonics, x-rays, and the like.

BRIEF DESCRIPTION OF THE DRAWINGS

The present invention will be further explained with reference to the appended Figures, wherein like structure is referred to by like numerals throughout the several views, and wherein:

FIG. 4 is a perspective view of an embodiment of a distal end portion of a delivery catheter or lumen and including a protruding guidance or targeting feature;

FIG. 5 is a perspective view of another embodiment of a distal end portion of a delivery catheter or lumen including a surface indicia or marker;

FIG. 6 is a front view of an indicator band located proximate to an injection port of an injection lumen of a fluid delivery system of the invention;

FIG. 7 is a rear view of the portion of a fluid delivery system illustrated in FIG. 6;

DETAILED DESCRIPTION

Figure 1:
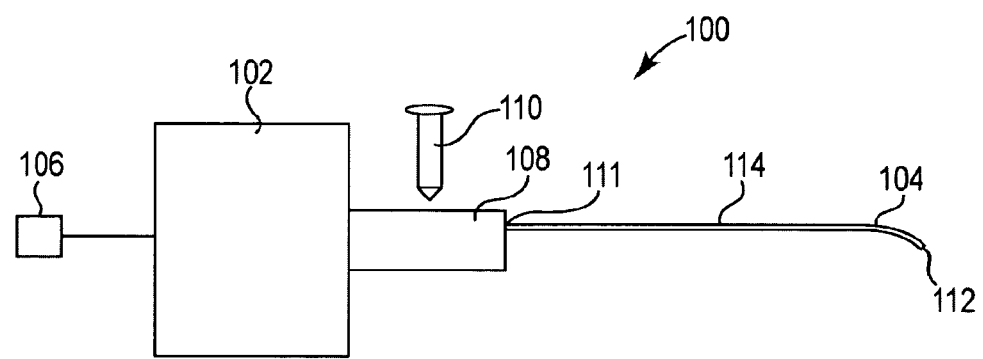
FIG. 1 is a schematic illustration of one embodiment of a needleless fluid delivery system for delivering a therapeutic fluid to a treatment location, in accordance with the invention.

The invention relates to devices and methods useful for injecting fluid into tissue for treatment. The fluid can be injected without the use of a needle and can therefore be referred to as a "needleless" fluid injection system. Needleless fluid injection systems of the invention can include one or more orifices that deliver fluid in the form of a jet or fluid stream without a needle passing into the tissue. This fluid is delivered at a pressure, velocity, and stream size that allow the fluid stream to pass through a tissue surface, penetrate into the bulk of the tissue below the tissue surface, and become dispersed as fluid particles within the tissue, such as in the form of a cloud of dispersed fluid particles or droplets. The type of tissue injected for treatment can be any amenable tissue, such as tissue at or near the urinary tract (e.g., tissue of the prostate, kidneys, ureters, urethral tissue, bladder, or other tissues such as heart tissue).

Needleless devices of the type described herein generally include a distal end and a proximal end. As used herein, a "distal end" of a device or system refers to an end area or portion of the device or system that can be introduced within a patient's body during a treatment procedure. For example, elongate shafts or catheters of the needleless injection systems of the invention generally include a distal end that is the first portion of the device that is inserted into the patient for treatment. The distal end may include functional features that operate on fluid or tissue during use, such as one or more orifices, delivery heads (e.g., end effectors, nozzles, etc.) that house one or more orifices, a frictional tissue holding tip, tissue tensioners, lighting or other optical features, steering features, and the like.

As used herein, a "proximal end" of an exemplary needleless device or system is the end that is generally opposite the distal end of that device or system. It is noted that each individual component of a system can include its own proximal and distal ends, while the overall system can also include proximal and distal ends. For one example, a needleless fluid injection system of the invention can include an injector body or console at a proximal end that remains external to the patient during use and an elongate shaft or catheter tube at a distal end. One or more injection orifices at the distal end can be in fluid communication with the console.

An exemplary console used with systems of the invention can include a housing that connects to or is otherwise (directly or indirectly) in fluid communication with an elongate shaft or catheter tube. The console can include fluid that can be pressurized by a pressure source to cause the fluid to flow through the shaft for injection into tissue at the distal end. A device can eject fluid from one or multiple ejection orifices that can be located at the distal end of the shaft or catheter tube.

The fluids that are injected into tissue using systems of the invention may be referred to as an "injectate" or "injection fluid", which may be any type of fluid such as a therapeutic fluid. A fluid stream or jet of injectate can be of a size (e.g., diameter), velocity, pressure, and volume to allow the fluid stream to penetrate directly through a tissue surface, then disperse within the tissue. The stream can be considered to be a relatively high velocity, high pressure, small diameter jet that after entry through a tissue surface, disperses within the tissue, preferably as a multi-directional collection of particles (e.g., a "cloud") or droplets within the bulk of the tissue. Exemplary pressures of a fluid at a pressure chamber can be at least 200 pounds per square inch (psi), and in some embodiments can range from 300 to 5000 pounds per square inch.

Referring now, to the Figures, wherein the components are labeled with like numerals throughout the several Figures, and initially to FIG. 1, one exemplary configuration of a needleless fluid delivery system 100 is schematically illustrated. Delivery system 100 generally includes an injection console 102, an injection chamber 108 in operative communication with the console 102, and a catheter tube or injectate shaft 104 that is also in operative communication with the console 102. The console 102 includes a user interface 106, which can be used for activating and controlling the activities of the various components of the delivery system 100. The user interface 106 can include an input means for selectively delivering a volume of pressurized fluid through the injection chamber 108. The user interface 106 may further include one or more actuatable devices, such as a foot petal, a hand activated controller, switches, buttons, and/or the like. It is also contemplated that the user interface 106 can include a touchscreen that is capable of receiving touch commands and may optionally include a display system for displaying information such as the mode of operation that is being used and/or certain operating parameters of the system.

Although console 102 can include a wide variety of features, any console used in the fluid delivery systems of the invention can generally include a housing, a pressure chamber, and a pressure source. A console can have any configuration, size, or design, ranging from a small, hand-held design to a relatively large floor or table-mounted console. The consoles can also include separate or separable components such as a pressure chamber or injection chamber that can be attached, used for an injection procedure, and detached and then optionally discarded or sterilized and reused. A shaft or catheter tube can also be attached to a console or a pressure chamber in a manner that facilitates separation and optional re-attachment or disposal.

With separable components, the injection chamber can be attached to a console housing and used to inject a first patient and/or a first injectate, and then the shaft or pressure chamber can be removed and discarded or sterilized. A second shaft or pressure chamber can then be attached to the console to treat a second patient or the first patient with second injectate or administer another treatment of the first injectate. The second patient or injectate can involve injection and treatment of the same type of tissue as the first patient or injectate, or of a new type of tissue than was treated in the first treatment. In this manner, separable and optionally disposable shaft or pressure chamber components of a needleless injection system can allow a console housing to be used multiple times to inject the same or different injectates to the same or different patients, and to the same or different types of body tissue, thereby providing an injection system that is flexible for use in a wide variety of situations and with a wide variety of fluids. Examples of system configurations, features and combinations of system features that can be useful according to the present description include U.S. Patent Application Publication No. 2006/0129125 (Copa et al.); U.S. Publication No. 2009/0312696, filed Jun. 27, 2008 (Copa et al.); PCT patent application Serial No. U.S.09/06390, filed Dec. 4, 2009 (Crank et al.), titled "Devices, Systems, and Related Methods for Delivery of Fluid to Tissue"; PCT patent application Serial No. U.S.09/06384, filed Dec. 4, 2009 (Crank), titled "Needleless Injection Device Components, Systems, and Methods"; PCT patent application Serial No. U.S.09/06383, filed Dec. 4, 2009 (Rykhus et al.), titled "Method and Apparatus for Compensating for Injection Media Viscosity in a Pressurized Drug Injection System", the entireties of which are all incorporated herein by reference.

The console can include actuating features to control distal end features of the system, such as steering a steerable distal end of a steerable shaft, actuating ejection of fluid, moving a moveable or extendable injectate shaft or one or more injection orifices relative to another shaft component such as a working shaft, and may further include optional ports to connect a console housing to auxiliary devices, electronics such as controls, optic features such as a lens, fiber optic, or electronic viewing mechanism to allow viewing through an optical feature (to view a location of delivery), and an actuating mechanism or pressure source for a tissue tensioner in the form of a mechanical tissue tensioner or an inflatable balloon. One or more attachment ports can optionally attach a console to an external and optionally remote component such as an external or remote pressure source, vacuum source, or an external or remote fluid reservoir to supply injectate or other fluid, such as to inflate a balloon. Embodiments of consoles can include a permanent or removable pressure chamber and a pressure source capable of pressurizing a fluid contained in the pressure chamber to cause the fluid to flow from the console, through a lumen in the shaft, and then through an injection orifice.

Examples of consoles, console features and combinations of console features that can be useful according to the present description are identified in Applicants' copending U.S. Patent Application Publication No. 2006/0129125; U.S. Publication No. 2009/0312696, filed Jun. 27, 2008 (Copa et al.); PCT patent application Serial No U.S.09/06383, filed Dec. 4, 2009 (Rykhus et al.), titled "Method and Apparatus for Compensating for Injection Media Viscosity in a Pressurized Drug Injection System"; and PCT patent application Serial No. U.S.09/06381, filed Dec. 4, 2009 (Crank), titled, "Devices, Systems and Methods for Delivering Fluid to Tissue", the entire disclosures of which are incorporated herein by reference.

Fluid can be provided to the system 100 by a fluid supply 110, which can be provided as a syringe that is manually activated, such as by physically pressing a plunger into a syringe barrel that is at least partially filled with fluid to push fluid from the syringe barrel. Alternatively, fluid supply 110 can have a different configuration than a syringe, and the fluid supply can be automatically or mechanically activated, such as with an electronic fluid supply controller and/or with one or more remote activation devices that can be manipulated by the user to move the plunger into and out of a syringe barrel. In yet another alternative, the fluid supply 110 is not a syringe, but instead includes a larger fluid source, such as a reservoir or other container that holds the fluid until it is provided to the injection chamber 108. Such a container can be positioned so that the fluid is gravity fed to the injection chamber, for example, or so that the fluid can be extracted using a vacuum source, for another example. With any of the different types of fluid supplies used with the systems of the invention, it is contemplated that an exact amount of fluid to be administered can be premeasured and provided to the system until that quantity of fluid is depleted and/or a predetermined amount of fluid can be extracted from a relatively large fluid supply.

A pressure chamber or injection chamber, such as injection chamber 108, can be a type of fluid chamber for containing one or more fluids (e.g., control fluid or injectate) for a purpose of placing the fluid under pressure to deliver the fluid through a lumen to a distal end of a shaft for ejection from an ejection orifice. Examples of pressure chambers include a syringe chamber and other variable volume spaces that can be used to contain and pressurize a fluid. Examples of variable volume pressure chambers include spaces that can exhibit a variable volume for increasing or decreasing the volume (and correspondingly decreasing or increasing pressure) within the variable volume chamber space. Such pressure chambers can include a plunger, piston, bellows, or other mechanisms. A pressure chamber can be pressurized by a pressure source attached to the plunger, bellows, or piston, etc., such that fluid contained in the pressure chamber is ejected under pressure. This pressurized fluid can be used for priming a device and/or for ejecting fluid from an ejection orifice for injection and/or to produce a control force, for example. A pressure source may be any source of energy (e.g., mechanical, electrical, hydraulically derived, pneumatically derived, or the like) such as a spring, solenoid, compressed air, manual syringe, electric power, hydraulic, pneumatic pressure sources, or the like. A pressure chamber may be a permanent or removable (i.e., attachable and detachable) component of a console housing.

In communication with a proximal end of the devices of the invention is an elongate shaft, which may also be referred to as an "injectate shaft." The injectate shaft extends from its proximal end, which is optionally removably connected to the console (or a component of the console such as a removable pressure chamber), to its distal end that can be placed in a patient during an injection procedure. The injectate shaft can be of various designs, minimally including an injection lumen to carry injectate from a proximal end of the injectate shaft to a distal end of the injectate shaft. Shafts for needleless devices as described are also described in PCT patent application Serial No. U.S.09/06390, filed Dec. 4, 2009 (Crank et al.), titled "Devices, Systems, and Related Methods for Delivery of Fluid to Tissue"; and in PCT patent application Serial No. U.S.09/06384, filed Dec. 4, 2009 (Crank), titled "Needleless Injection Device Components, Systems, and Methods"; the entireties of which are both incorporated herein by reference.

The injectate shaft can include structure such as sidewalls that define an injection lumen, the sidewalls being of sufficient strength to withstand operating pressures that are used to deliver injectate from the injection orifice at an elevated pressure that causes the injectate to be ejected from the injection orifice to penetrate a tissue surface and become injected into and dispersed below the tissue surface. An injectate shaft may therefore be made of a flexible material (e.g., a metal or polymeric tube) that can withstand such injection pressure, and may be prepared from materials capable of withstanding the pressure of an injection (e.g., nitinol, stainless steel, a non-reinforced polymer, or a reinforced (e.g., braided) polymer). The injectate shaft may be fabricated using suitable high strength polymers including, for example, polyimide, polyetherimide available from General Electric under the trade name "Ultem", and linear aromatic polymers for transporting the treatment fluid and the apposing jet medium to the treatment area. In some embodiments, the injectate shaft can be reinforced through the inclusion of materials including nano-particles, clays and/or glass. In some presently contemplated embodiments, the injectate shaft can be reinforced with one or more polymers such as, for example, tubes braided with Kevlar or other high-strength polymers. The injectate shaft can be fabricated so as to have a burst strength exceeding at least about 2,000 psi, for example. The nonmetal, polymeric tube-like device can be fabricated so as to have distention properties, wherein one or more orifices or jet ports located at a distal end of the polymeric tube-like device retains its shape and/or size without suffering swelling that can have a detrimental impact on a fluid jet used to deliver the therapeutic fluid at the treatment site.

Embodiments of the injectate shaft, such as injectate shaft 104, can be constructed of specific polymer materials having reinforcement materials therein or therealong. Other components of the delivery systems of the invention may also be made of materials that are specifically provided with reinforcement materials that are either imbedded into the components themselves or otherwise attached to those components. The reinforcement materials can be incorporated or mixed into the polymer material, or provided as a coating. The polymer materials can include poly ether ether ketone (PEEK), poly ether imide (PEI), poly sulfone (PS), poly ether sulfone (PES), poly ether ether sulfone (PEES), poly phenylene oxide (PPO), poly pheylene sulfide (PPS), poly ketone (PK), poly amide imide (PAI), for several examples. Such a material composition for the injectate shaft, or other components of the delivery system, can provide beneficial strength attributes to withstand the inherent pressures experienced in deploying a high-pressure injection catheter. In one embodiment, at least a portion of the injectate shaft can be made entirely of one or more of the above-listed materials.

An exemplary injectate shaft can include a sidewall that defines an outer shaft surface and an inner injector lumen, these being of continuous and relatively uniform dimensions of inner diameter, outer diameter, and wall thickness, along an entire length of the injectate shaft. Alternately, an injectate shaft, injector lumen, or sidewall, may change dimensions (e.g., wall thickness) along the length of the injectate shaft, with a larger wall thickness (e.g., greater outer diameter) at a proximal end and a thinner wall thickness (e.g., reduced outer diameter) at the distal end. A length of an injectate shaft can be any length that functions to place a proximal end at a console and a distal end at a desired tissue location.

The needleless injection systems of the invention may further include additional elongate shaft structures with desired functionality, a single example being a device referred to herein as "medical device shaft" or a "working shaft," which can be used to securely or moveably support or house an injectate shaft. For instance, an injectate shaft can be incorporated permanently or movably against or within a working shaft. In exemplary embodiments an injectate shaft can be loosely contained in a working lumen of a working shaft to allow movement of the injectate shaft length-wise and rotationally relative to the working shaft. Further, an injectate shaft may be capable of moving longitudinally within a working lumen to allow the injection lumen to be extended distally from an open end of a working lumen at a distal end of the working shaft. The working shaft can be used to manipulate and place the injection orifice of an injectate shaft at a desired location for treatment of tissue and can include any of a variety of optional functionalities such as steerability, an optical function, a tissue tensioner, or combinations of these, in addition to supporting the injectate shaft. An example of a particularly preferred working shaft can include features of a typical cystoscope, endoscope, ureteroscope, choledoscope, hysteroscope, catheter (e.g., urinary catheter), or the like, or other similar type of medical device shaft, including one or more features of flexibility, an optical function, a steerable distal shaft end, and a working lumen.

As discussed above, a distal end of an injectate shaft includes one or multiple injection orifices for ejecting fluid within a body of a patient. An injection orifice can be any form of opening, aperture, or orifice, such as an aperture or bore in an injectate shaft sidewall, or an aperture or bore in a nozzle, end effector, injection head, or other structure in communication with an injection lumen. Injection orifices can be located at relative locations and orientations along a length or circumference of an injectate shaft distal end to result in ejection and distribution of ejected fluid in different directions (e.g., circumferentially relative to the shaft), optionally or alternately at different distances along the length of the injectate shaft. An injection orifice can be directed at any angle relative to a longitudinal axis of a shaft, such as perpendicular, angled toward a distal end, or angled toward a proximal end.

According to exemplary injection methods and devices, an injection orifice may be located on a proximal side of a distal end tip at a location that allows the injection orifice and adjacent injectate shaft sidewall to contact a tissue surface as a longitudinal axis of a shaft that contains the injection orifice is positioned in an orientation that is parallel to the tissue surface. These device embodiments can be referred to as "side-fire" devices, for example. In certain embodiments of "side-fire" devices an injection orifice can be located a distance away from a distal end tip on a proximal side of the distal end tip so the injection orifice is located to contact tissue for injection by placing the shaft sidewall in contact with tissue.

Any high-pressure fluid delivery systems of that are used for needleless fluid delivery can further include guidance or targeting features that can be coupled with one or more corresponding visualization systems, such as an optic system, an endoscope, or another visualization system that can detect or otherwise locate the guidance or targeting features. Examples of injection catheters including these features are illustrated in FIGS. 4-7.

FIG. 4 illustrates a delivery catheter or lumen 400 that includes a working channel 406, an optical channel 408, and a guidance or targeting feature in the form of a protrusion 402 that extends from a distal end of an injection catheter or lumen 404. The protrusion 402 may be any desirable shape, size, and material, and while it should be large enough to be detectable via a visualization system, it should not be so large that it interferes with the placement of the device within the patient and/or other functionality of the device. It is contemplated that the protrusion 402 may be positioned in a different location relative to the distal end of the lumen 404 than shown, and that there may be multiple protrusions extending from a single lumen 404. These multiple protrusions may be positioned on the same or opposite sides of the lumen 404, and may be arranged in a visually detectable pattern, for example. This configuration may be particularly useful if the catheter or lumen 400 is adapted for a "side fire" spray or fluid throw, although it can also be adapted for use with other types of systems, such as "end fire" systems, for example. The protrusion is generally provided at a known or predefined location on or along the fluid delivery catheter or lumen 400 to promote positional guidance of the lumen 404 and accurate aim for the injectate spray path.

FIG. 5 illustrates a delivery catheter or lumen 420 that has a similar configuration to that of the delivery catheter or lumen 400 of FIG. 4. That is, the delivery catheter or lumen 420 also includes a working channel 426, an optical channel 428, and a guidance or targeting feature in the form of at least one surface indicia or marker 422 on the surface of a distal end of an injection catheter or lumen 424. The indicia or marker 422 may be any desirable shape or size that is detectable with a corresponding visualization system. Further, the indicia or marker 422 can be the same or a different material than the injection catheter or lumen 424 on which it is located, and it may be provided on the injection lumen 424 in any desirable application manner, such as printing, spraying, or otherwise providing a material to the surface of the injection lumen 424 in a controlled manner to achieve a desired placement. It is further contemplated that the indicia or markers 422 may alternatively or additionally be incorporated into the material of the injection lumen 424 themselves. The indicia or marker 422 should not be so large that it interferes with other visualization systems of the device and further should not be made of a material that adversely changes the flexibility or other physical characteristics of the device. It is also contemplated that the indicia or marker 422 may be positioned in a different location relative to the distal end of the lumen 424 than shown, and that there may be multiple markers or indicia on the surface of a single lumen 424. These multiple markers or indicia may be positioned on the same or opposite sides of the lumen 424, and may be arranged in a visually detectable pattern, for example. The indicia are generally provided at a known or predefined location on or along the fluid delivery catheter or lumen 420 to promote positional guidance of the lumen 420 and accurate aim for the injectate spray path.

Ultrasonic and/or x-ray guidance tools, systems and techniques can be used to facilitate tracking or visualization of any of the marking indicia described herein. In one embodiment, an x-ray marker will be a radiopaque material that can assist in distinguishing the marker and structure from the surrounding environment. Ultrasonic markers can have various density (e.g., micro- or macroscopically), texture, or coating attributes to distinguish the structures from the surrounding environment.

In another embodiment, a radiographic indicator band 442 can be disposed proximate an injection port of an injection lumen 440, as is illustrated in FIG. 6 (front view) and FIG. 7 (rear view). As shown, the indicator band 442 is located at a known position relative to an injection port 444 to allow for accurate detection of the location of the various features relative to each other. In this way, movement of the device will result in different visual appearances for each indicator band 442 under an x-ray system to provide increasingly accurate indications of the orientation and location of the lumen 440.

With these exemplary guidance and tracking features embodiments described herein, it is possible to measurably reduce the size of the overall injectate delivery system, and to provide a desirable targeted system to increase placement and accuracy. Further, because the guidance and tracking features can provide a known or predefined dimensional variable for the system, target tissue can be sized in accordance to its relationship with the particular guidance and tracking feature or system that is used.

Figure 8:
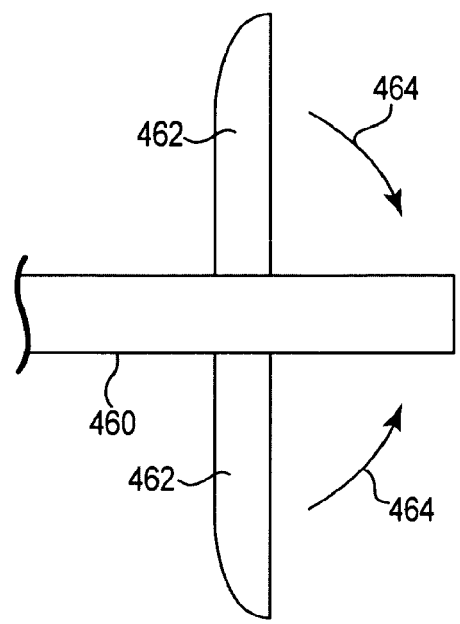
FIGS. 8 and 9 are schematic front views of a distal end of a fluid delivery system including a depth-controlling feature in its open and closed positions, respectively.
Figure 9:
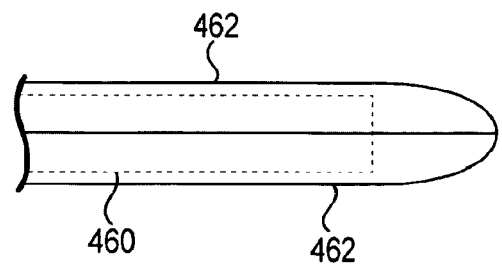

In order to position delivery systems of the invention in a desired location relative to the patient's anatomy, the devices of the invention can further be provided with depth-limiting or depth-controlling features at the distal end of the devices. These features can help to control or limit the indentation of the distal end tip of the device when positioning the injectate ports or orifices in a desired position to promote transverse or radial injectate dispersion from the ports. Referring particularly to FIGS. 8 and 9, one exemplary embodiment of a depth-controlling system is illustrated in its open position (FIG. 8) and in its closed position (FIG. 9), although it is understood that different configurations of depth-controlling systems may be attached or otherwise provided relative to the distal end of an injection lumen. In this particular embodiment, a folding flange system is illustrated as a collapsible and expandable member that is hinged or otherwise able to be flexed or rotated relative to the outer surface of the injection lumen.

With continued reference to the Figures, FIG. 8 illustrates a distal end of an injection lumen 460 and two flange portions 462 that are shown as extending from the longitudinal outer surface of the lumen 460 in a generally perpendicular direction. In one embodiment, this configuration is representative of the most extended position of the flange portions 462, although it is possible that the flange portions 462 have a range of motion that is greater than the approximate 90-degree range of motion shown. In this position, one or more surfaces of the flange portions 462 can be positioned relative to a location in a patient in order to accurately position the lumen 460 and any of its injection orifices. In order to collapse the flange portions 462, they can be moved in a direction indicated by arrows 464 toward the main body of the lumen 460.

In an initial deployment position, the flange portions 462 can be expanded manually or automatically (e.g., actively or passively) within the body lumen, as shown in FIG. 8. These flange portions 462 can be constructed of a shape memory or biased material that will urge the flange portions into their expanded or open position. Alternatively, an actuation mechanism can be included in operative communication with the flange portions 462 to control expansion and contraction. During deployment, the flange portions 462 can expand into abuttable contact with the surrounding tissue walls of the body lumen to obtain an ideal or predefined injection space between the injectate orifices and the tissue wall. This further provides positional anchoring of the device within the body lumen, and can ensure that the injectate ports are positioned correctly to promote transverse or radial injectate dispersion from the ports.

The flange portions 462 also provide a fixed reference for location and positioning of the injectate ports of the injection lumen 460 adjacent the desired target tissue. Once the injectate is applied to the target tissue, the flange portions 462 can be closed or collapsed to substantially follow the longitudinal length of the lumen 460 for removal of the device from the body lumen, as shown in FIG. 9. Various structures, mechanisms, and techniques can be employed to facilitate the expansion and collapsibility provided by the flange portions 462, including hinged members, shape-memory members, biasing members, pop-out members, inflatable members, and the like.

According to certain exemplary devices, a distal end of a shaft (injectate shaft, working shaft, or the like) can include a tissue tensioner, the tissue tensioner optionally being attached to the distal end of the shaft by a fastener that is attached to the tissue tensioner, such as part of a tissue tensioner assembly. A tissue tensioner can be located at a distal end of a shaft, somewhat near to an injection orifice. For example, a tissue tensioner can be located at a length-wise location along an injectate shaft that is the same length-wise location as the length-wise location of an injection orifice.

The tissue tensioner can comprise an expandable surface, e.g., a continuous expandable surface such as an inflatable balloon, or a non-continuous expandable surface such as an expandable metal (or plastic) cage or the like. The expandable surface can exhibit an expanded state and a non-expanded state. According to exemplary methods, a tissue tensioner can be placed in a body lumen in a non-expanded state and expanded within the lumen to the expanded state. In the expanded state, the tissue tensioner contacts an internal surface of the lumen to hold the distal end of the shaft and an associated injection orifice in place relative to desired tissue for injection. The tissue tensioner can optionally produce tension or strain on the tissue in a manner that can affect the manner in which an injected fluid stream penetrates the tissue surface and becomes distributed in the tissue upon injection. A tissue tensioner can facilitate a good result upon injection of fluid through luminal tissue by ensuring that the luminal tissue is fixed and includes a desired amount of tension for receiving an injection.

Examples of tissue tensioners include inflatable balloons located at a shaft distal end near an injection orifice (e.g., at the same length-wise location as the injection orifice), and mechanically extendable structures such as paddles, protrusions, levers, metal or plastic cages, metal or plastic springs or spirals, and the like, any of which can include a surface that can be extended (e.g., mechanically) from a distal end of a working shaft or injectate shaft to place pressure on internal tissue, e.g., on urethral tissue within the prostatic urethra or other luminal tissue. Tissue tensioners, device shafts, and related mechanisms and methods are described in Applicants' copending U.S. Patent Publication. No. 2006-0129125, and U.S. Patent Publication No. 2009-0312696, the entireties of which are both incorporated herein by reference.

When used within a lumen such as a urethra, a tissue tensioner can push luminal tissue (e.g., urethral tissue) away from the distal end of the shaft in a manner that causes the luminal tissue and an injection orifice to contact each other. This can be done, for example, by a balloon expanding from an opposite side of a shaft relative to an injection orifice to place pressure on luminal tissue located opposite from an injection orifice and to cause the injection orifice to contact adjacent luminal tissue, optionally to produce pressure, strain, or tension on the luminal tissue opposite of the balloon. A mechanical tensioner may be extended from a distal end of a shaft by use of an actuating mechanism such as a mechanical connection between the tissue tensioner and the proximal end of a device, such as at a working shaft proximal end. An inflatable balloon may be extended from a distal end of a shaft by inflating the balloon with pressurized fluid such as liquid, air, other gaseous fluids, or the like.

Referring again to FIG. 1 relative to one particular embodiment, a proximal or supply end 111 of the catheter tube or injectate shaft 104 extends from a distal end of the injection chamber 108. The shaft 104 may be permanently attached or connected to the injection chamber 108 so that the shaft 104 and chamber 108 are provided to the system as a single component. Alternatively, shaft 104 may be attachable and detachable from injection chamber 108, such as with quick connection fittings, so that the injection chamber 108 and shaft 104 are provided to the system as separate components. Injectate shaft 104 further includes a delivery or distal end 112, which is generally opposite the proximal or supply end 111.

Injectate shaft 104 may include multiple lumens, attachments, or other components that may extend along all or part of the length of the tube 104. Injectate shaft 104 may further comprise a number of different configurations, such as an endoscope or other catheter configuration, for example. Shaft 104 can further comprise a flexible, elongated attachment tube 114 to allow for easy positioning of the delivery or distal end 112 within the patient.

Delivery or distal end 112 of shaft 104 can comprise a number of different configurations, which can be designed to provide treatment to a specific location in the patient's body (e.g., a rectal treatment location, a gastrointestinal treatment location, a nasal treatment location, a bronchial treatment location, or an esophageal treatment location). The configuration of this distal end 112 is designed and/or selected to provide different types of treatment, such as can be provided by end-fire applicators or side-fire applicators.

Figure 2:
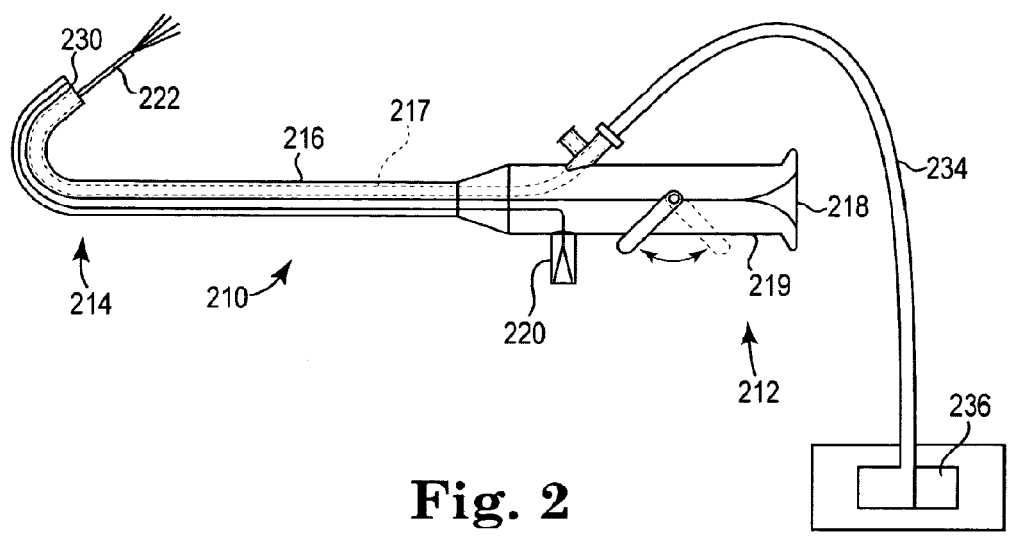
FIG. 2 is a schematic illustration of another embodiment of a needleless fluid delivery system and optical system, in accordance with the invention.

Another embodiment of an injection catheter device or system 210 is illustrated in FIG. 2. System 210 includes a proximal portion 212, a distal portion 214, and a shaft or body portion 216 between the proximal and distal portions. The proximal portion 212 generally includes a handle 218 and a connection port or assembly adapted to interconnect with a fluid source 236. The fluid source 236 is in operative and fluidic communication with the proximal portion via a conduit 234. The fluid source 236 can include a reservoir and a pressure source capable of pressurizing and advancing fluid contained in the fluid source. The fluid source 236 can be generally remote from the proximal portion 212 and/or the distal portion 214, or provided generally proximate or directly attached to the device components.

A working lumen or channel 217 extends within the shaft 216 and contains a fluid delivery lumen 222. This lumen 222 is adapted to move longitudinally along the length of the body 216 to allow its distal end to extend from the tip of the distal portion 214 as an orifice extension. The high-pressure injectate is delivered to the target tissue from the fluid delivery lumen 222. In particular, the injectate traverses from the fluid source 236, into the working channel 217, and out of the fluid delivery lumen 222. Shaft 216 can include a fiber optic feature 230, such as an endoscopic device that includes a light source 220 to transmit light to the distal portion 214, for example.

Figure 3:
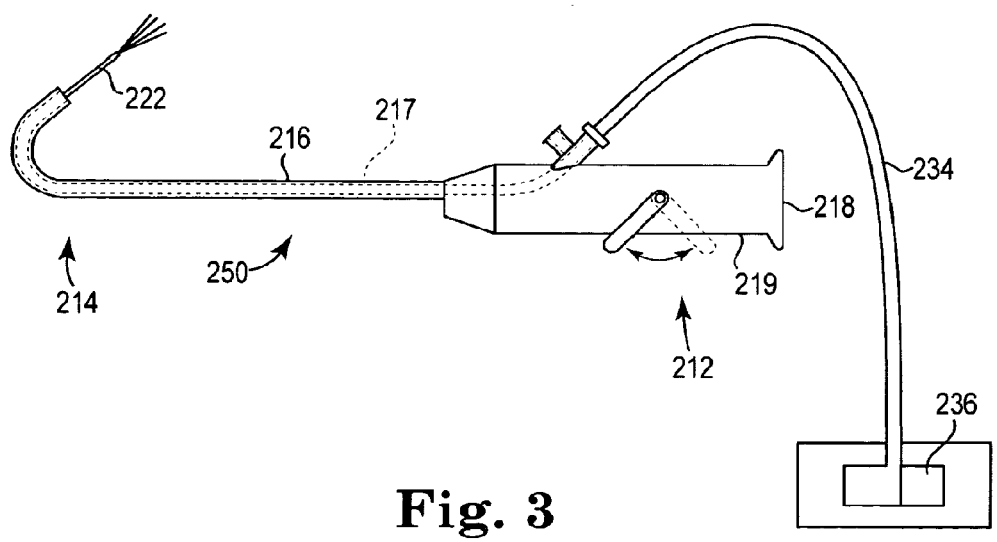
FIG. 3 is a schematic illustration of a needleless fluid delivery system that does not include an integrated or attached optic system.

In accordance with the invention, various embodiments of the fluid delivery systems described here can be configured without means of connecting or attaching an optic device (e.g., endoscope) to the injection catheter, as is illustrated with the delivery device 250 of FIG. 3. As shown in this Figure, many of the component features of the injection device or system 250 can be similar or identical in structure and functionality to those of the system 210 of FIG. 2 (e.g., the delivery lumen, fluid source, and the like). However, the fluid delivery system 250 does not include an integrated or attached optic feature 230 or a corresponding light source 220. This type of system or device can be utilized when optics are not needed for proper device positioning, such as for systems that instead use radiographic positioning techniques (e.g., a system that uses the radiographic features described and illustrated herein relative to FIGS. 6 and 7), ultrasonic positioning techniques, and the like. In this way, the flexibility and other features of the system 250 are not constrained by the structure of added optics components, and the system can therefore be designed to advantageously include additional torque control mechanisms and/or the system can be designed to be smaller than a comparable system that includes optics. In addition, the elimination of an optics system can reduce the overall cost of the injection device or system. In particular, exemplary torque control mechanisms that can be incorporated in the delivery system 250 can include one or more of a braided tube, coils, micro-machined tubes, kink-resistant tubing (KRT) features, and the like. The torque control structures can be constructed from a variety of different materials or combination of materials, such as metals, polymers, macroscopically and microscopically reinforced polymers, ceramics, and the like.

Figure 10:
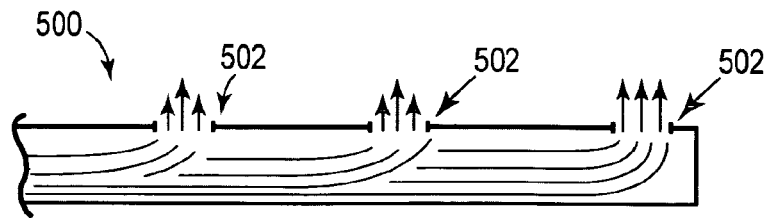
FIG. 10 is a schematic cross-sectional front view of a distal end portion of a fluid delivery lumen illustrating relatively non-uniform fluid flow through its orifices.

As described above, delivery systems may include lumens or catheters having one or more orifices for the delivery of fluid at a relatively high pressure to exit a fluid delivery lumen. Due to the inherent flow characteristics of a fluid delivery lumen having a smooth, continuous surface with multiple openings or orifices spaced from each other along its length, as is illustrated in FIG. 10, the volume of high-pressure fluid exiting each of the orifices can be different, depending on how far each of the orifices is spaced from the end of the device. For example, a distal end of a fluid delivery lumen 500 having a closed distal tip has multiple orifices 502 is shown in FIG. 10. The illustrated fluid flow depiction for such an embodiment indicates that a larger amount of injectate may exit the most distal orifice 502 as compared to the amount of injectate that may exit the orifices 502 that are spaced further from the closed distal tip.

Figure 11:
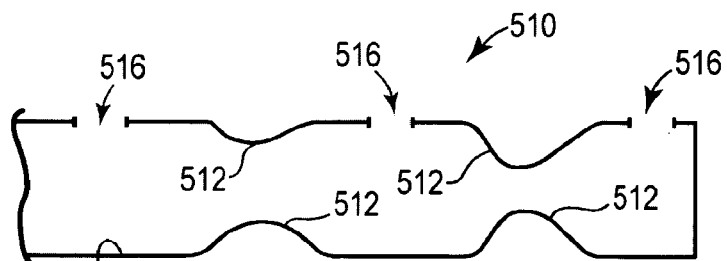
FIGS. 11-13 are schematic cross-sectional front views of distal end portions of fluid delivery lumens of the invention, illustrating various flow disruption injection systems for controlling and varying fluid flow through their orifices.
Figure 12:
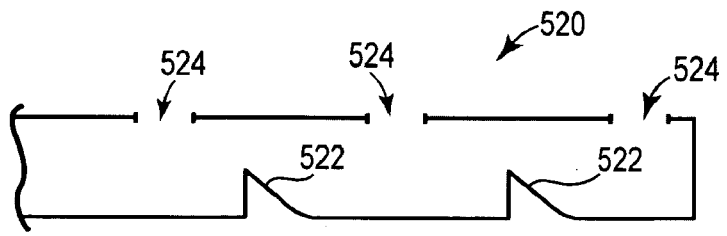
Figure 13:
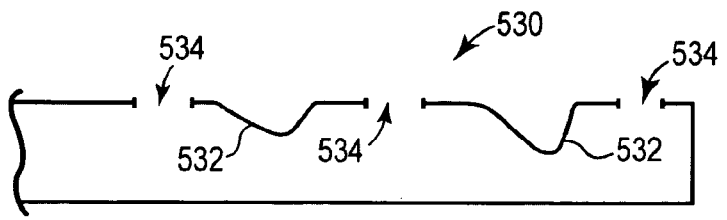

In order to controllably modify these fluid volume inconsistencies, exemplary embodiments of injection lumens are illustrated in FIGS. 11-13, which can include obstructions or protrusions extending into the interior space of the lumen, along with shape and spacing configurations for the lumen and corresponding orifices to achieve desired or predefined injectate fluid flow. FIG. 11 illustrates one exemplary embodiment of such a distal end area of an injection lumen 510, which is formed or shaped to include one or more interior flow features or protrusions 512 that controllably obstruct or modify the flow of fluid through the interior area of the lumen 510. These features 512 can be defined along an interior surface or wall 514 of lumen 510 and can be adjacent to similar or identical features 512 defined in the adjacent wall of lumen 510. Alternatively, the features 512 can be provided in offset configurations along the wall of the lumen 510. The features 512 are provided to generally restrict and direct fluid flow through the lumen 510 to achieve a desired and preferred injectate output through the orifices 516 (e.g., flow rate, viscosity, and uniformity of such flow characteristics). Various embodiments can include a design configuration for the features 512 and lumen 510 to promote increased injectate through one of the orifices 516 as compared to other adjacent orifices 516. For example, a central orifice can have a greater flow to promote injectate penetration along or within a central target location of a spherical object or body lumen.

FIGS. 12 and 13 illustrate additional exemplary embodiments of injection lumens 520 and 530, which include flow features or protrusions 522, 532, respectively. As set out above, these flow features or protrusions 522, 532 can take on a variety of shapes, sizes, and spacing configurations and can be arranged in a number of positions relative to their respective orifices 524, 534. For one example, flow features 522 of injection lumen 520 are all located on a side wall that is generally opposite to a wall through which the orifices 524 extend. In another example, flow features 532 of injection lumen 530 are all located on a side wall that also includes orifices 534 extending through it. Any combination of these arrangements is contemplated, such as is illustrated in FIG. 11, which includes flow features 512 on both walls that include orifices and walls that do not include such orifices. Each configuration can provide varying desired injectate flow outputs. It is understood that alternative lumens with various orifice and feature designs and relationships can be provided in accordance with the invention to achieve the specific desired injectate output for a particular application. It is further understood that the flow obstruction features illustrated are only intended to be exemplary and that a particular injection lumen may include more or less protrusions, that all of the protrusions of one injection lumen may be identical or differently sized or shaped, and the like.

The present invention has now been described with reference to several embodiments thereof. The entire disclosure of any patent or patent application identified herein is hereby incorporated by reference. The foregoing detailed description and examples have been given for clarity of understanding only. No unnecessary limitations are to be understood therefrom. It will be apparent to those skilled in the art that many changes can be made in the embodiments described without departing from the scope of the invention. Thus, the scope of the present invention should not be limited to the structures described herein, but only by the structures described by the language of the claims and the equivalents of those structures.

The invention claimed is:

1. A needleless fluid injection device comprising a flexible shaft comprising:
a proximal end,
a distal end,
a central longitudinal axis extending from the proximal end to the distal end.,
an injection catheter extending from the proximal end past the distal end of the shaft, wherein the injection catheter comprises a longitudinal axis that is radially offset from the central longitudinal axis,
at least one injection orifice extending through a wall of the injection catheter adjacent to the distal end of the shaft, and
at least one protrusion extending from a distal end of the injection catheter,
wherein the at least one protrusion is visually detectable as a guidance feature, and wherein the injection catheter comprises an elongated lumen that is open and free of obstructions along its length.

2. A needleless fluid injection device comprising a flexible shaft comprising:
a proximal end,
a distal end,
a central longitudinal axis extending from the proximal end to the distal end,
an injection catheter extending from the proximal end past the distal end of the shaft, wherein the injection catheter comprises a longitudinal axis that is radially offset from the central longitudinal axis,
at least one injection orifice extending through a wall of the injection catheter adjacent to the distal end of the shaft, and
at least one marker on a distal end of the injection catheter that is visually distinct from an outer surface of the injection catheter.

3. The injection device of claim 2, wherein the at least one marker comprises surface indicia on the outer surface of the injection catheter.

4. A needleless fluid injection device comprising a flexible shaft comprising:
a proximal end,
a distal end,
a central longitudinal axis extending from the proximal end to the distal end,
an injection catheter extending from the proximal end past the distal end of the shaft, wherein the injection catheter comprises a longitudinal axis that is radially offset from the central longitudinal axis,
at least one injection orifice extending through a wall of the injection catheter adjacent to the distal end of the shaft, and
at least one protrusion extending from a distal end of the injection catheter, wherein the at least one protrusion is visually detectable as a guidance feature, and wherein the at least one protrusion comprises a plurality of protrusions arranged in a visually detectable pattern relative to the at least one injection orifice of the injection catheter.

5. A needleless fluid injection device comprising a flexible shaft comprising:
a proximal end,
a distal end,
a central longitudinal axis extending from the proximal end to the distal end,
an injection catheter extending from the proximal end to the distal end of the shaft, wherein the injection catheter comprises a longitudinal axis that is radially offset from the central longitudinal axis,
at least one injection orifice extending through a wall of the injection catheter adjacent to the distal end of the shaft, and
a radiographic indicator band positioned proximate at least one of the injection orifices of the injection catheter.

6. The injection device of claim 2, wherein the at least one marker comprises a plurality of markers arranged in a visually detectable pattern relative to the at least one injection orifice of the injection catheter.

7. The injection device of claim 2, wherein the at least one marker is incorporated into a material that comprises the injection catheter.

8. The injection device of claim 1, wherein the longitudinal axis of the injection catheter is generally parallel to the central longitudinal axis of the flexible shaft from the proximal end of the flexible shaft to the distal end of the injection catheter.

9. The injection device of claim 8, further comprising an optical channel having an optical channel longitudinal axis that is adjacent to the longitudinal axis of the injection catheter and radially offset from the central longitudinal axis.

10. The injection device of claim 1, wherein the injection catheter is nonexpandable along its length from the proximal end of the flexible shaft to its distal end.

11. The injection device of claim 4, wherein the longitudinal axis of the injection catheter is generally parallel to the central longitudinal axis of the flexible shaft from the proximal end of the flexible shaft to the distal end of the injection catheter.

12. The injection device of claim 11, further comprising an optical channel having an optical channel longitudinal axis that is adjacent to the longitudinal axis of the injection catheter and offset from the central longitudinal axis.

* * * * *